US 7,189,403 B2

(12) United States Patent
Despres et al.

(10) Patent No.: US 7,189,403 B2
(45) Date of Patent: Mar. 13, 2007

(54) ATTENUATED FLAVIVIRUS STRAINS CONTAINING A MUTATED M-ECTODOMAIN AND THEIR APPLICATIONS

(75) Inventors: Philippe Despres, La Garenne-Colombes (FR); Adeline Catteau, Savigny-sur-Orge (FR)

(73) Assignee: Institut Pasteur, Paris (FR)

( * ) Notice: Subject to any disclaimer, the term of this patent is extended or adjusted under 35 U.S.C. 154(b) by 148 days.

(21) Appl. No.: 10/608,029

(22) Filed: Jun. 30, 2003

(65) Prior Publication Data
US 2004/0266987 A1   Dec. 30, 2004

(51) Int. Cl.
*A61K 39/12*   (2006.01)
*A61K 39/00*   (2006.01)
*A61K 39/385*   (2006.01)
*C12Q 1/70*   (2006.01)

(52) U.S. Cl. .............................. 424/218.1; 424/192.1; 424/196.11; 435/5

(58) Field of Classification Search ............... 530/300, 530/350; 424/218.1, 204.1; 435/6, 5
See application file for complete search history.

(56) References Cited

U.S. PATENT DOCUMENTS 6,180,604 B1 *   1/2001   Fraser et al. .................. 514/12

OTHER PUBLICATIONS

Chang et al. "Recent advancement in flavivirus vaccine development," Expert Rev. Vaccines 3(2), 199-220 (2004).*
Meeting report: Review on Flavivirus Vaccine Development; Proceedings of a meeting jointly organised by the World Health Organization and the Thai Ministry of Public Health, Apr. 26-27, 2004, Bangkok, Thailand. Vaccine 23 (2005) 2689-2695.*
U.S. Appl. No. 10/608,029, filed Jun. 30, 2003, Despres, et al.
U.S. Appl. No. 10/608,147, filed Jun. 30, 2003, Despres, et al.

* cited by examiner

*Primary Examiner*—Bruce R. Campell
*Assistant Examiner*—M. Franco Salvoza
(74) *Attorney, Agent, or Firm*—Oblon, Spivak, McClelland, Maier & Neustadt, P.C.

(57) ABSTRACT

The present invention relates to nine residue peptides (ApoptoM) from flavivirus M ectodomain able to modulate specifically the apoptotic activity of diverse flavivirus, to pharmaceutical composition comprising the same and their use for the treatment and/or the prevention of flavivirus-linked infections and cancers.

15 Claims, 9 Drawing Sheets

A.

B.

C.

A.

| Category | Fusion protein-expressing cells with apoptotic nuclei (%) |
|---|---|
| Control | ~4 |
| DEN-1 | ~21 *** |
| DEN-2 | ~21 *** |
| DEN-3 | ~15 *** |
| DEN-4 | ~17 *** |
| JE | ~12 *** |
| WN | ~12 *** |
| YF | ~12 *** |

B.

| Category | Fusion protein-expressing cells with apoptotic nuclei (%) |
|---|---|
| Control | ~4 |
| $C^{95-114}$-EGFP-$M^{1-40/YF.wt}$ | ~12 *** |
| $C^{95-114}$-EGFP-$M^{1-40/YF.17D}$ | ~4 n.s. |

FIGURE 3

| DEN-2 ectoM | mutants |
|---|---|
| ¹SVALVPHVGMGLETRTETWMSSEGAWKHVQRIETWILRHP⁴⁰ | M 1-40/DEN-2 |
| ¹SVALVPHVGMGLETRTETWMSSEGAWKHVQ³⁰ | M 1-30/DEN-2 |
| ¹SVALVPHVGMGLETRTETWM²⁰ | M 1-20/DEN-2 |
| ¹⁰GMGLETRTETWMSSEGAWKHVQ³⁰ | M 10-30/DEN-2 |
| ¹⁰GMGLETRTETWMSSEGAWKHVQRIETWILRHP⁴⁰ | M 10-40/DEN-2 |
| ²⁰MSSEGAWKHVQRIETWILRHP⁴⁰ | M 20-40/DEN-2 |
| ³²IETWILRHP⁴⁰ | M 32-40/DEN-2 |

Séquence du plasmide p[95-114] EGFP [$M_1$-$M_{40}$]DEN-2 (I36F)

Séquence en 5' du gène EGFP du plasmide pEGFP-N1 (Clontech, # 6085-1, Gene Bank accession # U55762)

591 601 611 621 631 641 651 661 671 → EGFP

5' G CTA GCG CTA CCG GAC TCA GAT CTC GAG CTC AAG CTT CGA ATT CTG CAG TCG ACG GTA CCG CGG GCC CGG GAT CCA CCG GTC GCC ACC ATG

Nhe I (G CTA GC) … Sma I (CC CGG G)

Séquence du virus DEN-1 souche BR/90 en 5' du gène de l'EGFP séquence DEN-1 →

*Peptide signal de prM*

M N R R K R S V T M L L M L L P T A L A H P P V A T M

5' G CTA GCA ATG AAC AGG AGG AAA AGA TCC GTG ACC ATG CTC CTC ATG CTG CTG CCC ACA GCC CTG GCC CGG GAT CCA CCG GTC GCC ACC ATG

Nhe I (G CTA GC) … Sma I (CC CGG G)

Séquence en 3' du gène EGFP du plasmide pEGFP-N1

1380 1390 1400 1410

L A M' E E L 'Y K ochre

5' CTC GGC ATG GAC GAG CTG TAC AAG TAA AGC GGC CGC ACT CTA

BsrG I (TG TAC A) … Not I (GC GGC CGC)

Séquence de l'ectodomaine de la protéine M du virus DEN-2 muté I36F en 3' du gène EGFP

PHVGMGLETRTETWMSSEGAWKHVQRIETW 1380 1390

L A M' E E L 'Y R S V A L V | F L R H P opal

5' CTC GGC ATG GAC GAG CTG TAC AGA TCA GTG GCA CTC GTT ___ TTC TTG AGA CAT CCA TGA GCG GCC GCG ACT C

BsrG I (TG TAC A) … Not I (GCG GCC GC)

FIGURE 7

ATTENUATED FLAVIVIRUS STRAINS CONTAINING A MUTATED M-ECTODOMAIN AND THEIR APPLICATIONS

The present invention relates to attenuated flavivirus strains, able to be used as vaccines, which contain, in the M ectodomain, mutations leading to flavivirus strains which have lost their cytotoxicity or which have a significantly reduced cytotoxicity. The present invention also relates to small peptides of a length of at most nine amino acids from flavivirus M ectodomain with mutations which lead to the lost or the reduction of the cytotoxicity of the flavivirus strain containing such a modified (mutated) peptide; thus such mutated small peptides are able to be used to construct attenuated flavivirus strains. The invention also relates to nucleic acid molecules containing said peptides, to pharmaceutical compositions comprising the same and their use for the prevention of infections.

Mosquito-borne flaviviruses such as the dengue (DEN), Japanese encephalitis (JE), Saint Louis encephalitis (SLE), West Nile (WN) and yellow fever (YF) viruses may cause epidemic disease outbreaks in humans. Infected patients may exhibit a wide range of acute diseases, from nonspecific febrile illness to severe hemorrhagic manifestations (DEN and YF) or encephalitic syndromes (JE, SLE and WN). Flaviviruses (family Flaviviridae) are single-stranded, enveloped RNA viruses (5, 41). The virion consists of three structural proteins: C (core protein), M (membrane protein) and E (envelope protein) (5, 41). The translation of genomic RNA generates a large polyprotein precursor, which is cotranslationally processed by host cell- and virus-encoded proteases to yield the individual structural and non-structural viral proteins. The structural proteins are C, prM (the intracellular precursor of M), and E (5, 41). E and prM are both type I transmembrane glycoproteins (5, 41). The prM glycoprotein consists of a long ectodomain followed by a transmembrane-anchoring region (5, 41). The carboxy-terminal region of the prM protein gives rise to the small membrane (M) protein (7–9 kDa). The mature M protein consists of a 40 amino acid ectodomain followed by the transmembrane-anchoring region including two transmembrane domains (TMDs) (5, 41). The E protein consists of a long ectodomain followed by a stem-anchor region (5, 41). The first steps of flavivirus assembly take place in association with the membranes of the endoplasmic reticulum (ER). The virion is first assembled as an immature particle, in which prM is non-covalently associated with E in a heterodimeric complex. Late in virus morphogenesis, prM is processed by subtilisin-like proteases to generate the mature M protein in the exocytic pathway of the trans-Golgi network (5, 41). Three-dimensional imaging of the structure of the DEN virion, showing the location of the M protein with respect to the E homodimer, was recently carried out (25). Several studies have shown that the M ectodomain induces a neutralizing antibody response (3, 47).

Recent advances in cell biology have resulted in advances in our understanding of the mechanisms of virus-induced cell death, which determine the outcome of flavivirus infection (36, 37, 39, 42, 45). Cytotoxicity seems to result from apoptosis, which may contribute to the clinical manifestations associated with flavivirus infection (8, 13). Apoptosis is an active process of cell death involving a number of distinct morphological changes including cell shrinkage, phosphatidylserine (PS) externalization, fragmentation of the cell nucleus, chromatin condensation, protein cross-linking and apoptotic body formation (21, 24). Apoptosis is induced via the activation of intracellular signaling systems, a number of which converge on mitochondrial membranes to induce their permeabilization (21, 24). The morphological and biochemical changes associated with apoptosis are orchestrated by the activity of a family of cysteine proteases called caspases (14, 41). Mitochondria membrane permeabilization plays an essential role in apoptosis, releasing caspase-activating proteins that are normally confined to the mitochondrial intermembrane space (2, 9, 21). Members of the Bcl-2 family have been shown to exhibit both anti-apoptosis and proapoptotic activities (1). For example, increased levels of Bcl-2 lead to cell survival whereas excess of Bax is associated with apoptosis.

All four serotypes of DEN virus (DEN-1, DEN-2, DEN-3, and DEN-4), and the JE, SLE, WN, and YF viruses have been reported to trigger apoptosis in host cells (36, 37, 39, 42, 45). The precise mechanisms by which flaviviruses induce the death of infected cells are unclear, but it is thought that virus infection may activate biochemically different apoptotic pathways converging in the modification of mitochondrial function. The intracellular production of viral proteins has been shown to be essential for the induction of apoptosis by flaviviruses (12–14, 39, 40). The E and NS3 proteins may be involved in the induction of apoptosis by the tick-borne flavivirus Langat (39, 40). Detailed studies of molecular interactions between DEN-1 virus and host cells have led to the identification of viral proteins that may influence DEN virus-induced apoptosis (14).

WO 01/96376 discloses a pro-apoptotic frgment of 40 amino acids (ectodomain) from the dengue virus M protein and corresponding to residues 206–245 of said M protein. Said fragment,—included in a plasmid, p[95–114]EGFP [206–245], encompassing the DEN-1 virus strain BR/90 encoding the C protein residues 95 to 114 upstream of the EGFP gene and the sequence of the DEN-1 virus strain FGA/89, encoding the M protein residues 206 to 245 downstream of the EGFP gene-, induces rapid apoptosis in Neuro 2a, HepG2, HeLa and Vero cells as early as 20 hours posttransfection.

WO 01/96376 describes also a series of deletion variants of said 40 amino acids protein M ectodomain, which were constructed in view to find the elements which contribute to the efficient death-inducing activity of the M ectodomain. The results obtained with said variants show that transient expression of the deletion variants of the chimeric protein [95–114]EGFP[206–245]DEN-2 demonstrated that amino acids M10 to M40 of the M ectodomain ([95–114]EGFP [M10–>M40]DEN-2) significantly contribute to the efficient formation of the fluorescent mass in the secretory pathway.

Pursuing their works, the Inventors have now found unexpectedly that, in a carboxy-terminal amino acid fragment of the M ectodomain (M32–M40, in reference to the M ectodomain protein of DEN-1 virus GenBank accession number AAB27904) comprising between 6 and 9 amino acids, the mutation of the M36 amino acid residue by any amino acid except Leu, Ala or Ile residue and preferably a phenylalanine residue leads to flavivirus strains which have lost their cytotoxicity or in which the cytotoxicity is significantly reduced, in particular, when M36 is a phenylalanine residue. Therefore modified dengue strains and more specifically modified DEN-2 strains containing such a modified M ectodmain may advantageously be used as a vaccine against flavivirus infections.

More specifically, the Inventors have detected that mutations, more specifically in position 5 of said peptides, lead to good vaccine candidates.

No biological function has yet been assigned to the flavivirus membrane (M) protein. It has been shown that the 40 amino-acid ectodomain of the DEN M protein has pro-apoptotic properties. The transport of the M ectodomain from the Golgi apparatus to the plasma membrane is essential for its pro-apoptotic activity. The M ectodomain of wild-type strains of Japanese encephalitis, West Nile and Yellow fever (YF) viruses also have proapoptotic properties, suggesting that M protein may play an important role in the pathogenicity of flaviviruses. Remarkably, the M ectodomain has a great potential for apoptosis induction in transformed and tumor cells of various origins.

The results of experiences made by the Inventors, operating with truncated forms of the DEN-2 ectodomain indicate that the nine carboxy-terminal amino acids of the M ectodomain (M32–40) constitute an intrinsic apoptotic sequence. The discovery of M32–40 brings to light a role for the small membrane M protein in DEN virus pathogenicity. Detailed comparison indicated that M32–40 of the four serotypes of DEN where more than 75% identical. Searches on nucleotide and protein databases showed that the nine-residue sequence responsible for the cytotoxic effect of the M ectodomain displayed no obvious similarity with any known cellular protein. Viscerotropic YF virus causes damage to liver cells in humans and hepatocytic apop-tosis has been observed in infected livers. Two live attenuated vaccine strains, 17D and French neurotropic virus (FNV) are known to have the ability to cause viscero-tropic disease. Comparison of the genomes of the YF vaccine strains 17D and French neurotropic virus (FNV) with the parental and other wild-type YF viruses revealed a common difference at position M36: the isoleucine residue at this position in the wild-type YF virus (Asibi) was replaced by a phenylalanine (17D vaccine strain) during attenuation. The Inventors demonstrate for the first time that the 136F substitution observed in YF vaccine strains abolishes the death-promoting activity of the YF M ectodomain. The 136F substitution also results in a reduction of the cytotoxicity of the DEN-2 ectodomain. Thus residue M36 not only plays an essential role for the efficient induction of apoptosis by peptides M32–40 containing it, but also the residue M36 is critical fot the attenuation of viscerotropic flaviviruses.

Therefore, in a first aspect, the present invention relates to an isolated and purified peptide, characterized in that it has the following formula:

X1-X2-X3-X4-X5-X6-X7-X8-X9, wherein:

X1 is absent or represents an amino acid selected in the group consisting of non-charged polar amino acids and non-polar amino acids, X2 is absent or represents an amino acid selected in the group consisting of acidic amino acids, non-charged polar amino acids and non-polar amino acids, X3 is selected in the group consisting of basic amino acids, non-charged polar amino acids and non-polar amino acids, X4 is W, X5 represents any amino acid except A, L or I, X6 is a non-polar amino acid, X7 is a basic amino acid X8 is selected in the group consisting of basic amino acids and non-charged polar amino acids and X9 is absent or represents an amino acid selected in the group consisting of basic amino acids and non-polar amino acids.

The amino acids (or amino acid residues) described herein are preferred to be in the "L" isomeric form. However, residues in the "D" isomeric form can be substituted for any L-amino acid residue, as long as the desired functional property is conserved. In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

The following gives the list of the amino acids in each of the group specified here above:

Amino acids with nonpolar R groups
Alanine, Valine, Leucine, Isoleucine, Proline, Phenylalanine, Tryptophan, Methionine, Cysteine Amino acids with uncharged (or non-charged) polar R groups
Glycine, Serine, Threonine, Tyrosine, Asparagine, Glutamine Amino acids with charged polar R groups (acid amino acids) (negatively charged at pH 6.0)
Aspartic acid, Glutamic acid Basic amino acids (positively charged at pH 6.0)
Lysine, Arginine, Histidine (at pH 6.0)

Particularly preferred conservative substitutions are:
  Lys for Arg and vice versa such that a positive charge may be maintained;
  Glu for Asp and vice versa such that a negative charge may be maintained;
  Ser for Thr such that a free —OH can be maintained; and
  Gln for Asn such that a free $NH_2$ can be maintained.

According to an advantageous embodiment of the invention, said peptide is selected in the group consisting of peptides of 6–9 amino acids wherein X5 represents F.

The invention also includes any functional derivative of the peptides as defined above, comprising one or more modifications which do not affect substantially the biological activities of the initial peptide.

Such modifications include for example: replacement of one or more of the amide bond by a non-amide bond, and/or replacement of one or more amino acid side chain by a different chemical moiety, and/or protection of the N-terminus, the C-terminus, or one or more of the side chain by a protecting group, and/or introduction of double bonds and/or cyclization and/or stereospecificity into the amino acid chain to increase rigidity, and/or binding affinity and/or enhance resistance to enzymatic degradation of the peptides. Since all the variations are known in the art, it is submitted that a person skilled in the art will be able to produce, test, identify and select other peptides according to the present invention. For instance, in some cases it may be possible to replace a residue in the L-form by a residue in the D-form or the replacement of the glutamine (Q) residue by a pyroglutaminic acid compound.

The peptides according to the invention refer to peptides which have the following activities:
biological activity: they do not have a pro-apoptotic activity or they have a reduced apoptotic activity compared with cytotoxic wild strain derived peptides;
antibody binding activity: they are recognized specifically by a monoclonal or polyclonal antibody, which may be induced, preferably with a peptide as defined hereabove conjugated with a carrier protein such as BSA (bovine serum albumin) or KLH (keyhole limpet haemocyanin).

The biological activity of the instant peptides can be verified by the absence of in situ detection of apoptotic cells, which is well-known by a person skilled in the art. This technique can be performed for example on transformed or tumor cell lines such as HeLa cells which are initially transfected by a recombinant vector containing the sequence encoding prM translocation signal fused in frame with the sequence encoding the N-terminal fragment of the enhanced green fluorescent protein (EGFP) and downstream the sequence encoding a peptide according to the invention and appropriate regulation sequences.

The instant peptides are useful for preparing attenuated flaviviruses strains.

In addition to said use, the instant peptides are useful as complementary tools to uncover mechanisms of action and unknown function of the M ectodomain of flavivirus. For instance, for the screening of molecules (able to treat infections induced by a flavivirus) i.e. which modulate the cytotoxic activity of the instant peptides.

The peptides of the present invention may be prepared by any suitable process. Preferably, it is obtained by chemical synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups. For solid phase synthesis the technique described by Merrifield (J. Am. Chem. Soc., 1964, 85, 2149–2154) may be used.

The peptides of the present invention may also be obtained by genetic engineering technology. A typical example comprises culturing a host cell containing an expression vector comprising a nucleic acid sequence encoding said peptide, under conditions suitable for the expression of the peptide, and recovering the peptide from the host cell culture. The peptide may be included in a fusion protein by cloning a cDNA into an expression vector in frame with a polynucleotide coding for the peptide of the invention. Alternatively, multimer of identical or different peptides can also be produced by expressing a polynucleotide coding for multiple copies of a monomer, or coding for different monomers.

The invention also provides, in a second aspect, attenuated flavivirus strains, which include the nucleotide sequences encoding the peptides as defined here above with the proviso that said attenuated flavivirus strain is different from the Yellow fever strains having the following GENPEPT accession numbers: AF052437, AF052438, AF052439, AF052440, AF52442, AF052444, AF052445, AF052446, AF052447, AF094612, X03700 (strain YF 17D), U17066, U17067, U21055, X15062.

More specifically, the instant invention concerns attenuated dengue virus strains, which include the nucleotide sequences encoding the peptides as defined here above.

Said attenuated flavivirus strains are advantageously DEN-2 strains obtained by site-directed mutagenesis, by PCR on cDNA blot followed by sequencing et multiplication of the selected viruses. Some of the techniques which may be used are reviewed in Pugachev K V et al. (Internat. J. Parasitol., 2003, 33, 567–582).

Modified viruses according to the invention are useful:
for preventing Flavivirus-linked infections as vaccines,
for the screening of molecules (able to treat infections induced by a flavivirus) i.e. which modulate the cytotoxic activity of the instant peptides,
for producing monoclonal antibodies to be used as a diagnostic tool in the detection of flavivirus infections in a biological sample; moreover, knowing that the instant peptides correspond to a conserved sequence in the flavivirus phylogeny, the obtained antibodies may advantageously be used for the detection of flavivirus, whatever the variant.

Thus, the invention also provides a polynucleotide encoding either the peptide according to the invention, as well as the complement of said polynucleotide or the attenuated flavivirus according to the invention.

Definitions

The positions of the M-ectodomain are given in reference either to DEN-1 M-ectodomain or to DEN-1 M-protein; therefore, positions 237–245 are equivalent to positions 32–40 (FIG. 4).

An apoptotic molecule is a molecule which influences or modifies apoptosis.

A pro-apoptotic molecule is a molecule which induces apoptosis (directly or indirectly).

An anti-apoptotic molecule is a molecule which inhibits apoptosis (directly or indirectly).

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide" is defined as a molecule comprising two or more ribonucleotides, preferably more than three. Its exact size will depend upon many factors which, in turn, depend upon the ultimate function and use of the oligonucleotide.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis.

A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., SAMBROOK et al., "Molecular Cloning: A Laboratory Manual" (1989); "Nucleic Acid Hybridization" [B. D. Hames & S. J. Higgins eds. (1985)]; B. Perbal, "A practical Guide To Molecular Cloning" (1984).

It should be appreciated that also within the scope of the present invention are the biological uses of the DNA sequences encoding said peptides, but which are degenerate to the DNA encoding said peptides. By "degenerate to" is meant that a different three-letter codon is used to specify a particular amino acid. It is well known in the art that the following codons can be used interchangeably to code for each specific amino acid:

| Amino acid | Codons |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Therefore, the invention provides the nucleotide sequences encoding the peptides as defined here above, including all possible examples of nucleotide sequences encoding these peptides which result from the degeneration of the genetic code.

Nucleic acids of the invention may be obtained by the well-known methods of recombinant DNA technology and/or chemical DNA synthesis.

The invention also provides recombinant vectors comprising a polynucleotide encoding a peptide or an attenuated flavivirus strain of the invention.

Preferably, said recombinant vector contains a polynucleotide encoding an attenuated flavivirus strain including the polynucleotide sequence encoding a peptide according to the invention and more specifically a peptide in which X5=F.

Said plasmid has been deposited at the Collection Nationale de Cultures de Microorganismes, 28 Rue de Docteur Roux, F-75724 Paris Cedex 15, on Jun. 25, 2003 under the number 1-3061.

The invention also comprises a prokaryotic or eukaryotic host cell transformed by a vector of the invention.

The invention further concerns polyclonal and monoclonal antibodies, and preferably monoclonal antibodies, raised specifically against the peptides or the attenuated flavivirus of the instant invention and their utilization for prevention of disease and diagnostic purposes. Antibodies which react specifically with the instant peptides are generated by using methods well-known in the art. Examples of such methods are disclosed in Antibodies, A Laboratory Manual, Harlow and Lane, Cold Spring Harbor Press, 1988. Said antibodies have the advantage to be able to distinguish virulent wild type strains from attenuated strains according to the invention.

The invention further concerns a pharmaceutical composition comprising an effective amount, for inducing protection against flavivirus infections, of a peptide of the invention or a polynucleotide encoding the same or a polynucleotide encoding an attenuated flavivirus strain according to the invention, and at least one pharmaceutically acceptable carrier.

More specifically, the invention further concerns an immunogenic composition able to protect against a flavivirus infection comprising a modified DEN-2 strain of flavivirus, wherein the sequence encoding the M protein comprises in position 241 a codon for any amino acid residue except A, L or I; it comprises preferably a F residue. Such a modified strain has an attenuated virulence and may therefore be used as a vaccine.

The invention further concerns the use of a peptide, a polynucleotide or a recombinant vector of the invention for the preparation of a medicament for the prevention and/or the treatment of a pathological condition selected from the group consisting of non-specific febrile illnesses to severe hemorrhagic manifestations, encephalitic syndromes, these pathological conditions being linked to Flavivirus infection.

The invention further concerns a method for the preparation of attenuated strains of flavivirus wherein said attenuation is obtained by expression of a mutated M ectodomain protein of said flavivirus, in which the amino acid sequence between position 237–245 of said M ectodomain protein (DEN-1 numbering) is a peptide as defined hereabove.

The invention further concerns the direct detection method of a flavivirus infection, which comprises:
contacting a biological sample to be analysed or a culture medium supposed to eventually contain flavivirus antigens with antibodies according to the invention, optionally labelled, and
detecting the antigen-antibody complex eventually formed by any means.

The invention further concerns the serological detection of a flavivirus infection, which comprises:
contacting a biological sample with a solid support on which peptides according to the invention are bound, and
detecting the eventually formed antigen-antibody complexes by any means.

The invention also concerns a method for the vaccinal survey of a patient, comprising the detection in a biological fluid of said patient of antibodies directed against an attenuated flavivirus strain as defined here above.

The invention further concerns chimeric flavivirus, wherein the M ectodomain includes a peptide as defined here above.

The present invention will be further illustrated by the additional description and drawings which follow, which refer to examples illustrating the properties of the instant peptides. It should be understood however that these examples are given only by way of illustration of the invention and do not constitute in anyway a limitation thereof.

FIG. 1 illustrates a schematic representation the EGFP-tagged DEN-I proteins. The fusion proteins consisting of the ER targeting sequence ($C^{95-14}$, designed SS) of prM, the full-length M ($M^{1-74}$), the ectodomain ($M^{1-40}$) of the M protein, the stem-anchor ($E^{392-487}$) and the stem ($E^{392-487}$) of the E protein fused to EGFP, are depicted. The transmembrane domain (TMD) is shown. The fusion proteins are not drawn to scale. The names of fusion proteins are indicated on the left.

FIG. 2 shows that DEN-1 M ectodomain has proapoptotic activity. HeLa cells were transfected with plasmids encoding the fusion proteins described in FIG. 1. Transiently transfected HeLa cells were harvested after 25 hours (A and C) or at the times indicated (B). Fixed cells were stained with Hoechst 33258 (A and B) or assayed by TUNEL (C). Fusion proteins were detected by monitoring the autofluorescence of EGFP. Fusion protein-expressing cells with nuclear DNA nicks were monitored by TUNEL assay. Each experimental point represents the mean±the standard deviation (SD) of results obtained from three separate chambers. Fusion proteins were compared statistically with $C^{95-114}$-tagged EGFP: not significant (n.s., P>0.05) or significant (*P<0.05; P<0.01; *P<0.001), according to Fisher and Yates's t tests.

FIG. 3 shows that the M ectodomains from apoptosis-inducing flaviviruses have proapoptotic properties. HeLa cells were transfected with constructs encoding $C^{95-114}$-EGFP (control, open box), $C^{95-114}$-EGFP-$M^{1-40/DEN-1}$ (DEN-1), $C^{95-114}$-EGFP-$M^{1-40/DEN-2}$ (DEN-2), $C^{95-114}$-EGFP-$M^{1-40/DEN-3}$ (DEN-3), $C^{95-114}$-EGFP-$M^{1-40/DEN-4}$ (DEN-4), $C^{95-114}$-EGFP-$M^{1-40/JE}$ (JE), $C^{95-114}$-EGFP-$M^{1-40/WN}$ (WN), or $C^{95-114}$-EGFP-$M^{1-40/YF.wt}$ (YF) (A), or with plasmids encoding $C^{95-114}$-EGFP (control; open box), $C^{95-114}$-EGFP-$M^{1-40/YF.wt}$ ($M^{1-40/YF.wt}$) or $C^{95-114}$-EGFP-$M^{1-40/YF.17D}$ ($M^{1-40/YF.17D}$) (B). Transfected HeLa cells were stained with Hoechst 33258 after 25 hours of transfection and examined for changes in nuclear morphology. The percentages of fusion protein-expressing cells displaying chromatin condensation are indicated. Each experimental point represents the mean±the SD of results obtained from three separate chambers. Fusion proteins were compared statistically with their respective controls.

FIG. 4 shows that the nine carboxy-terminal amino acids of the M ectodomain constitute a proapoptotic sequence. (A) Amino acid sequence alignments for mutant proteins, the names of which are shown on the right (SEQ ID NO:23 and sections of SEQ ID NO:3). (B) and (C) Transfected HeLa cells were assayed for apoptotic nuclear fragmentation after 25 hours of transfection (B) or for the early stage of apoptosis after 20 hours (C). (B) HeLa cells were stained with Hoescht 33258 and examined for chromatin condensation. $C^{95-14}$-tagged EGFP (Control; open box) served as a negative control. The percentages of fusion protein-expressing cells with apoptotic nuclei are indicated. Each experimental point represents the mean± the SD of results obtained from three separate chambers. Statistical analysis for fusion proteins were carried out by comparison with the control. (C) The rate of early apoptosis was analyzed by Annexin V binding, as assessed by flow cytometry analysis. Apoptosis in fusion protein-expressing HeLa cells was defined as EGFP-positive cells that bound Annexin V-APC but excluded PI. For each sample, data from 10,000 EGFP-positive cells were collected. The percentages of $M^{1-40}$-and $M^{32-40}$-expressing cells labeled with Annexin V are indicated (square).

FIG. 5 shows that the residues M-34 to M-39 contribute to the death-promoting activity of the M ectodomain. (A) Amino acid sequence (SEQ ID NOS: 24, 25, 23 and 29) alignments of $M^{1-40/DEN-2}$, $M^{1-40/YF.17D}$ and mutants $M^{1-40/DEN-2}$ (F36) and $M^{1-40/YF.17D}$ ($T^{34}$, $I^{36}$, $L^{37}$, $H^{39}$). Identical amino acids are indicated (asterisks). The amino acid substitutions are underlined and indicated in bold. (B) After 25 hours of transfection, fusion protein-expressing HeLa cells were stained with Hoechst 33258 and examined for chromatin condensation. The percentages of fusion protein-expressing cells with apoptotic nuclei are indicated. Each experimental point represents the mean ± the SD of results obtained from three separate chambers. Fusion proteins were compared statistically with $C^{95-114}$-tagged EGFP (Control; open box).

FIG. 7 represents the plasmid sequence p[95–114]EGFP [$M_1$-$M_{40}$]DEN-2 (I36F) (SEQ ID NOS:30–36).

EXAMPLE 1

Figure 1:
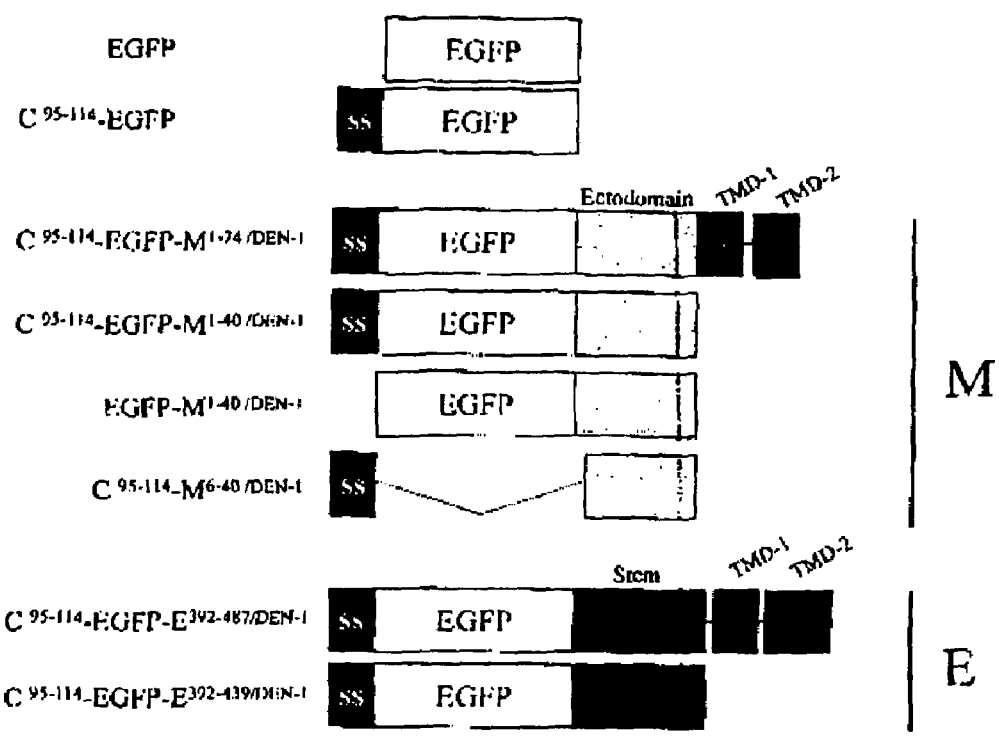

Expression of the M Ectodomain Leads to Apoptosis

1) Materials and Methods 1.1) Materials

Cell Lines and Viruses

The human epithelial HeLa cell line was cultured in DMEM supplemented with 10% fetal calf serum (FCS) and 2 mM L-glutamine.

The South-American strain of DEN-1 virus FGA/89 has the GenBank accession number: AF226687.

Plasmids

Viral RNA was extracted from purified flavivirus or infected cell lysates using the RNA plus reagent (Quantum Bioprobe). The RNA was reverse-transcribed using the Titan One-Step RT-PCR kit (Roche Molecular Biochemicals) according to the manufacturer's instructions. All constructs were verified by automated sequencing.

The BR/90 cDNA encoding residues C-95 to C-114 (amino acid residues are numbered as for DEN-1 virus [11]) was introduced into NheI/SmaI-digested pEGFP-N1 (this plasmid pEGFP-N1 was purchased from BD Clontech BioSciences), the eukaryotic expression vector containing the gene encoding the enhanced green fluorescent protein (EGFP). The resulting plasmid, $pC^{95-114}$-EGFP, encodes the prM translocation signal followed by six vector-specified residues, EPPVAT, fused in-frame with the N-terminus of EGFP.

Synthetic oligonucleotide primers containing recognition sites for BsrGI (5' primer) and NotI (3' primer), were used to amplify specific sequences of the flavivirus genome encoding the full-length M (residues M-1 to M-74) (see Table I below).

TABLE 1

| M | 5' primer |
|---|---|
| DEN-1 | 5'-gacaaacgttccgtggctctgtgacacacgtgggacttggtctag-3' (SEQ ID NO:1) |
| DEN-2 | 5'-cacagaagactgtacagatcagtggcactcgttcc-3' (SEQ ID NO:3) |
| DEN-3 | 5'-agacgcgtgtacagatcagtggcgttagctccccatgtcgcc-3' (SEQ ID NO:5) |
| DEN-4 | 5'-agacgagtgtacagctcagtagctttaacaccacattcgg-3' (SEQ ID NO:7) |
| JE | 5'-aagcgaatgtacagatccgtgtcggtccaaacacatggggagag-3' (SEQ ID NO:9) |
| WN | 5'-agacgcatgtacaggtcactgacagtgcag-3' (SEQ ID NO:11) |
| YF | 5'-aggaggttgtacagggccattgacttgcctacgcatgaaaacc-3' (SEQ ID NO:13) |

TABLE 1-continued

| M | 3' primer | Strain |
|---|---|---|
| DEN-1 | 5'-ctattcccagcggccgctaggccattgatggtg-3' (SEQ ID NO:2) | FGA/89 |
| DEN-2 | 5'-atattcctagcggccgctatgtcattgaaggagcg-3' (SEQ ID NO:4) | Jamaica |
| DEN-3 | 5'-gtttccgcggccgccacatcttcatgtcataggtggggtaacc-3' (SEQ ID NO:6) | H-87 |
| DEN-4 | 5'-tgtttccgcggccgccgcatcgtcatccgtaggatgggcga-3' (SEQ ID NO:8) | H-241 |
| JE | 5'-attgccgcggccgcgacaatttcaactgtaagccggagcgacc-3' (SEQ ID NO:10) | Nakayama |
| WN | 5'-cattccgcggccgctctagctgtaagctgg-3' (SEQ ID NO:12) | IS-98-ST1 |
| YF | 5'-tgtcagtgcggccgctgcagtgtcatgagtaggccggaccaac-3' (SEQ ID NO:14) | 17D-204 |

| Mutants | 5' primer | |
|---|---|---|
| $M^{1-30/DEN-2}$ | 5'-ttttggcagtacatcaatgggcg-3' (SEQ ID NO: 15) | |
| $M^{1-20/DEN-2}$ | 5'-ttttggcagtacatcaatgggcg-3' (SEQ ID NO:15) | |
| $M^{9-30/DEN-2}$ | 5'-ttttggcagtacatcaatgggcg-3' (SEQ ID NO:15) | |
| $M^{9-40/DEN-2}$ | 5'-tggttctgtacatgggaatgggactggagacacg-3' (SEQ ID NO:18) | |
| $M^{20-40/DEN-2}$ | 5'-actgaaatgtacatgtcatcagaagggcctgg-3' (SEQ ID NO:20) | |
| $M^{32-40/DEN-2}$ | 5'-atgtcctgtacattgaaacttggatcttgag-3' (SEQ ID NO:21) | |

| Mutants | 3' primer | Plasmid[1] |
|---|---|---|
| $M^{1-30/DEN-2}$ | 5'-aagatcgcggccgcaattcactggacatgtttccaggc-3' (SEQ ID NO:16) | $M^{1-40/DEN-2}$ |
| $M^{1-20/DEN-2}$ | 5'-tttccgcggccgctctgatcacatccatgtttcagttcag-3' (SEQ ID NO:17) | $M^{1-40/DEN-2}$ |
| $M^{9-30/DEN-2}$ | 5'-aagatcgcggccgcaattcactggacatgtttccaggc-3' (SEQ ID NO:16) | $M^{9-40/DEN-2}$ |
| $M^{9-40/DEN-2}$ | 5'-tcttgcagttcattcagggcaccg-3' (SEQ ID NO:19) | $M^{1-40/DEN-2}$ |
| $M^{20-40/DEN-2}$ | 5'-tcttgcagttcattcagggcaccg-3' (SEQ ID NO:19) | $M^{1-40/DEN-2}$ |
| $M^{32-40/DEN-2}$ | 5'-tcttgcagttcattcagggcaccg-3' (SEQ ID NO:19) | $M^{1-40/DEN-2}$ |

[1] $pC^{95-114}$-EGFP-$M^{1-40DEN-2}$ or $pC^{95-114}$-EGFP-$M^{9-40/DEN-2}$

Plasmid $pC^{95-114}$-EGFP-$M^{1-74}$ was constructed by digesting the RT-PCR products with BsrGI and NotI and by introducing the resulting fragment into BsrGI/NotI-digested $pC^{95-114}$-EGFP, such that the full-length M was directly fused inframe with the carboxy-terminal end of EGFP. Plasmid $pC^{95-114}$-EGFP-$M^{1-40}$ was constructed by amplifying flavivirus cDNAs encoding the M ectodomain (residues M-1 to M-40) by PCR using $pC^{95-114}$-EGFP-$M^{1-74}$ as a template and a set of 3' primers containing a stop codon (TGA) followed by a NotI restriction site. The PCR products were introduced into $pC^{95-114}$-EGFP, such that the flavivirus M ectodomains were produced as fusions with EGFP.

Figure 6:
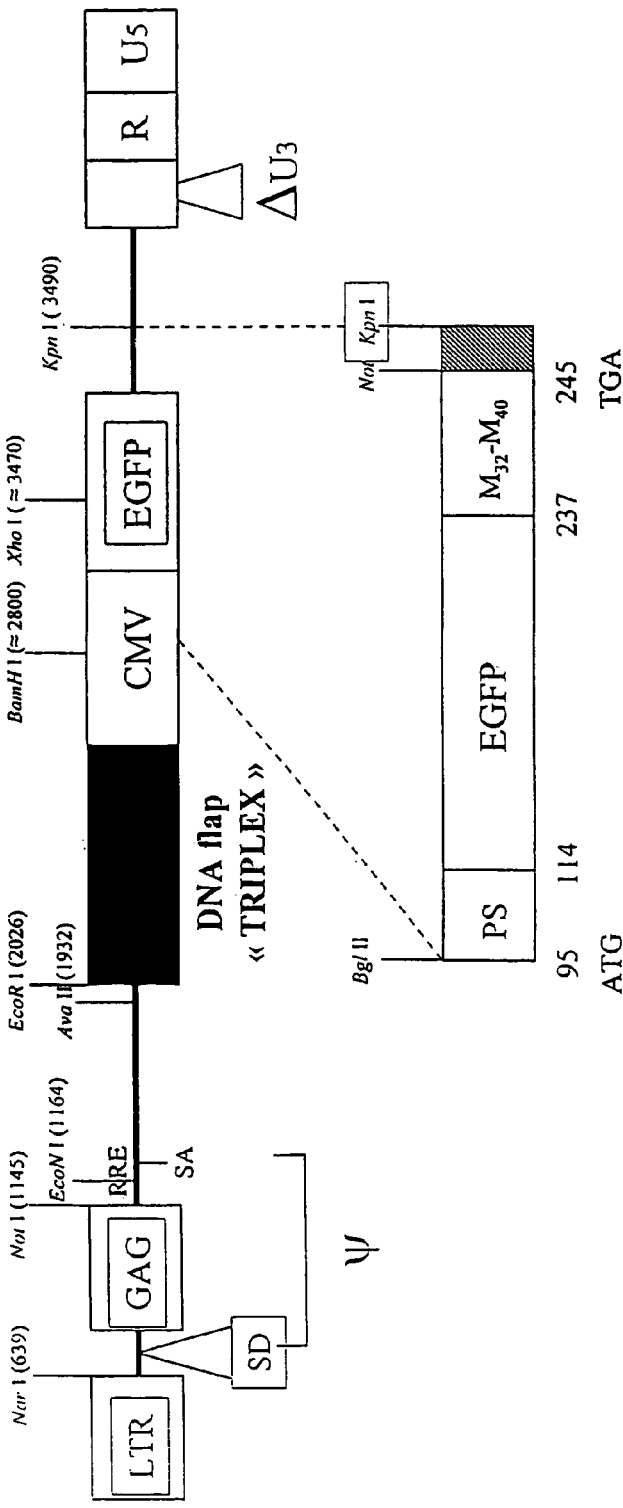
FIG. 6 represents the restriction card of plasmid Trip Δ U3 CMV[95–114]EGFP[$M_{32}$-$M_{40}$] DEN-2.
Figure 6:
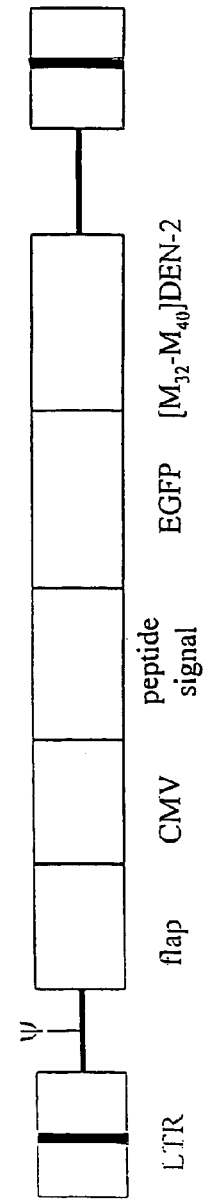

Plasmid Trip Δ U3 CMV[95–114] EGFP[$M_{32}$-$M_{40}$] DEN-2 derives from plasmid Trip A U3 CMV GFP (Zennou et al., Cell, 2000, 196, 173–185) (CNCM n° I-2330). Said plasmid contains upstream gene EGFP, the cDNA of virus DEN-1 BR/90 encoding amino acids 95–114 of the dengue polyprotein and downstream said EGFP gene, cDNA of DEN-2 Jamaïca virus encoding amino acids 237–245 of said polyprotein as it emerges from FIG. 6. Transfer vectors able to form triplex structures are more specifically described in the Institut Pasteur International PCT Application WO 99/55892.

To construct a series of mutants with deletions in the DEN-2 M ectodomain ($M^{1-40/DEN-2}$), PCR fragments were generated using $pC^{95-114}$-EGFP-$M^{1-40/DEN-2}$ or $pC^{95-114}$-EGFP-$M^{9-40/DEN-2}$ as a template and primers containing recognition sites for BsrGI and NotI and a stop codon TGA (see Table I). The PCR products encoding mutant proteins were inserted into $pC^{95-114}$-EGFP downstream from the EGFP gene.

1.2) Method

Transient Transfection of Cells

Cells were distributed to Permanox Lab-tek chambers (Nalge Nunc International) or 6-well plates. After one day of culture, cell monolayers were transfected with 6 µg of plasmid per $10^6$ cells in the presence of FuGene 6 transfection reagent (Roche Molecular Biochemicals), according to the manufacturer's instructions. The fusion proteins were detected by monitoring the autofluorescence of EGFP.

In Situ Detection of Apoptotic Cells

The cells were fixed by incubation with 3.2% paraformaldehyde (PFA) in PBS for 20 min. The Inventors have investigated the nuclear changes associated with apoptotic cell death by incubating fixed cells with 0.1 µg/ml Hoechst 33258 (Sigma) in 0.1% citrate buffer (pH 6.0) for 10 min at room temperature. Cells were considered to be apoptotic if their nuclei displayed margins and chromatin condensation. At least 200 transfected cells from three independent cell chambers were used to quantify apoptosis. Apoptosis-induced DNA breaks were detected by the deoxyterminal transferase-mediated dUTP nick-end labeling (TUNEL) method as previously described (11). Nuclear TUNEL assay was performed with CY™ 3 conjugated-streptavidin (Jackson Immunoresearch). Cells were examined under an AXIOPLAN 2 fluorescence microscope (Zeiss). Images were processed on a computer, using RS Image 1.07, SimplePCI 5.1, Adobe Photoshop and Powerpoint software.

2) Results

The inventors have shown that the infection of host cells with DEN-1 virus isolate FGA/89 leads to apoptosis (12–14). They investigated the role of DEN-1 envelope glycoproteins in the induction of apoptosis by examining the stable cell line N2aprM+E which carries the FGA/89 cDNA encoding prM plus E under the control of an inducible exogenous promoter (7). Apoptosis was observed in induced N2aprM+E cells, suggesting that prM and E are involved in DEN virus-induced apoptosis.

The Inventors have investigated whether the anchor regions of DEN envelope glycoproteins were involved in apoptosis induction. The FGA/89 cDNAs encoding the carboxy-terminal regions of prM and E were inserted into a mammalian expression vector under the control of the human cytomegalovirus IE promoter. EGFP-tagged DEN proteins were constructed by fusing viral gene sequences immediately downstream from the reporter gene encoding EGFP (FIG. 1).

As the carboxy-terminal part of prM contains M, the EGFP-tagged M proteins contained either the complete M protein, including the TMDs (residues M-1 to M-74), or only the M ectodomain (residues M-1 to M-40) (FIG. 1). The EGFP-tagged E proteins included either the stem alone (residues E-392 to E-439) or the stem-anchor region (residues E-392 to E-487) of the E protein (FIG. 1). The sequence encoding the internal signal sequence ($C^{95-114}$), which is located at the junction of the DEN-1 C and prM proteins and directs the translocation of prM into the lumen of the ER (5, 41), was inserted upstream from sequences encoding the EGFP-tagged DEN proteins (FIG. 1).

The Inventors assessed the production of the chimeric proteins by transient transfection of HeLa cells. After 15 hours of transfection, transiently-transfected HeLa cells were assayed for EGFP production by direct fluorescence analysis. Upon transfection with pEGFP-N1, autofluorescence of EGFP was observed in more than 50% of the HeLa cells. Western blot assays with anti-EGFP antibodies showed that the electrophoretic mobility of EGFP in $C^{95-114}$-EGFP-expressing HeLa cells was similar to that of the EGFP encoded by the control plasmid, pEGFP-N1. This demonstrates that proteolytic cleavage occurred at the junction between the prM translocation signal and EGFP.

Figure 2:
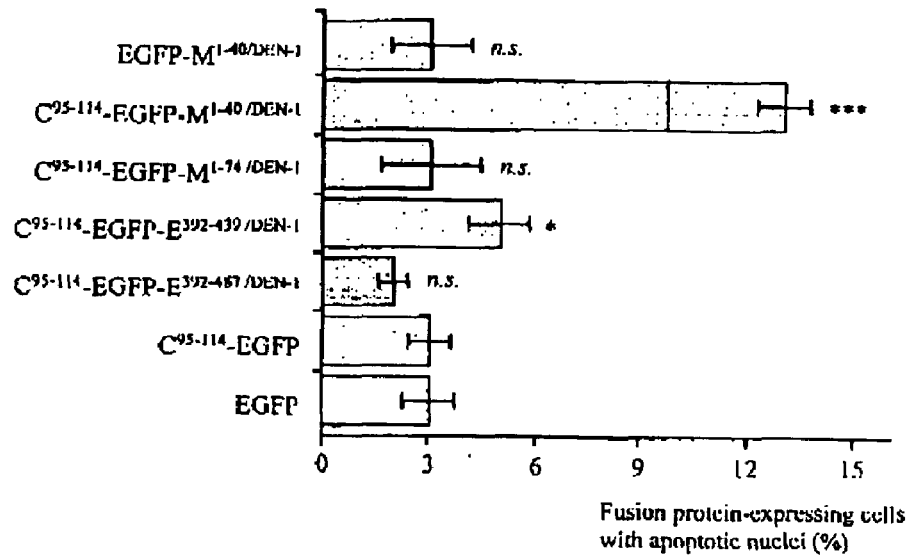
Figure 2:
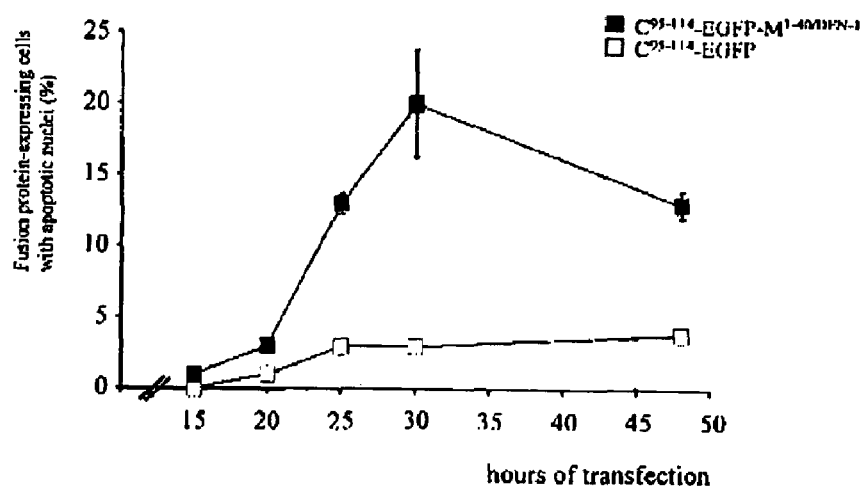
Figure 2:
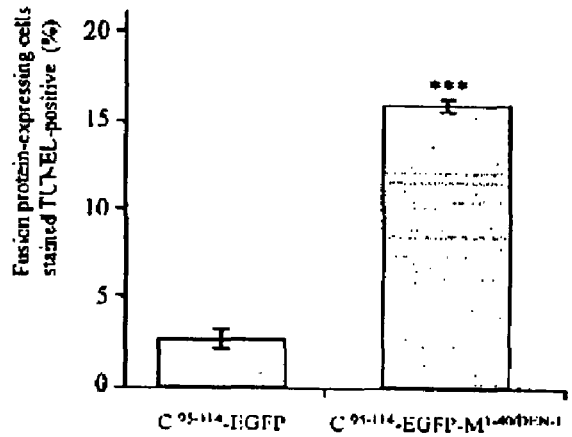

The Inventors have evaluated the ability of EGFP-tagged DEN proteins to induce apoptosis by means of transient transfection experiments with HeLa cells. Surprisingly, they found that the production of $C^{95-114}$-EGFP-$M^{1-40/DEN-1}$, which includes the M ectodomain, resulted in cell death (FIG. 2A). Approximately 15% of $M^{1-40/DEN-1}$-expressing HeLa cells displayed chromatin condensation after 25 hours of transfection, with a peak of 20% at 30 hours, as assessed by Hoechst 33258 staining (FIG. 2B). To confirm that apoptosis occurred in HeLa cells producing $C^{95-114}$-EGFP-$M^{1-40/DEN-1}$, $M^{1-40/DEN-1}$, apoptotic DNA fragmentation was assessed by the nuclear TUNEL assay (25). The Inventors observed apoptotic nuclear fragmentation in more than 15% of $M^{1-40/DEN-1}$-expressing cells after 25 hours of transfection (FIG. 2C). The proportion of apoptotic cells determined by the TUNEL method correlated well with that determined by counting cells with nuclei displaying apoptotic morphology. As production of the full-length M protein or the stem-anchor region of the E protein did not result in cell death (FIG. 2A), the cytotoxicity of the M ectodomain was not due to an overexpression artifact after transfection.

To exclude the possibility that EGFP contributes to the death-promoting activity of the EGFP-tagged $M^{1-40/DEN-1}$ protein, the deletion mutant protein $C^{95-114}$-$M^{6-40/DEN-1}$ consisting of residues M-6 to M-40 directly fused to the prM translocation signal (FIG. 1) was constructed. Upon transfection with $pC^{95-114}$-$M^{6-40/DEN-1}$, approximately 10% of HeLa cells displayed chromatin condensation after 25 hours of transfection. These results suggest that the M ectodomain (hereafter referred to as ecto-M) of DEN-1 virus induces apoptosis in transfected HeLa cells.

EXAMPLE 2

Proapoptotic Properties of the M Ectodomains of JE, WN, and YF Viruses

1) Materials and Methods 1.1) Materials

Viruses

The DEN-1 virus strains FGA/89 and BR/90, the DEN-2 virus strain Jamaica (GenBank accession number: M20558), the DEN-3 virus strain H-87 (GenBank accession number: NC 001475), the DEN-4 virus strain H-241 (GenBank accession number: NC 002640), the JE virus strain Nakayama (JE virus strain SA[V], GenBank accession number: D90194), and the WN virus strain IS-98-ST1 (GenBank accession number: AF481864) were produced in cultured Aedes pseudocutillaris AP61 mosquito cells, as previously described (11). The YF virus strain 17D-204 Pasteur (GenBank accession number: X15062) was produced in human SW13 cells (10).

Expression Vectors

Mutant protein $C^{95-114}$-EGFP-$M^{1-40/YF.wt}$ was generated using p$C^{95-114}$-EGFP-M $^{1-40/YF.17D}$ as a template and the 3' primer 5'-AGAGTCGCGGCCGCAAATCAGGGGTTC-CTCACCAACCATCTCTC-3' (SEQ ID NO:26) extended by 20 nucleotides to include a stop codon (TGA) followed by a NotI restriction site.

1.2) Methods

The software used for sequence comparison was the program CLUSTAL W (53, 54).

2) Results

As the DEN-1 M ectodomain induced apoptosis, the Inventors have investigated whether the M ectodomains of other DEN serotypes and of other apoptosis-inducing flaviviruses, such as wild-type strains of JE, WN and YF viruses also cause cell death. Production of the various EGFP-tagged M ectodomains was confirmed by Western blotting. All flavivirus M ectodomains induced apoptosis after 25 hours of transfection (FIG. 3A), suggesting that the proapoptotic properties of ecto-M are conserved among apoptosis-inducing flaviviruses. The M ectodomains of DEN-1 and DEN-2 viruses were the most potent inducers of apoptosis.

Comparison of the genomes of the YF vaccine strains 17D and French neurotropic virus (FNV) with the parental and other wild-type YF viruses revealed a common difference at position M-36: the leucine residue at this position in the wild-type YF viruses ($M^{1-40/YF.wt}$) was replaced by a phenylalanine ($M^{1-40/YF.17D}$) during attenuation (35). Unlike EGFP-tagged $M^{1-40/YF.wt}$, $C^{95-114}$-EGFP-$M^{1-40/YF.17D}$ did not trigger apoptosis in transfected HeLa cells (FIG. 3B). Thus, the $I^{36}F$ substitution observed in vaccine strains abolishes the death-promoting activity of the YF M ectodomain.

EXAMPLE 3

Determination of a Six-Nine Residues Sequence Required for the Induction of Apoptosis by the M Ectodomain 1) Materials and Methods 1.1) Materials Expression Vectors Mutant protein $C^{95-114}$-EGFP-$M^{1-40/YF.17D}$ ($T^{34}$, $I^{36}$, $L^{37}$, $H^{39}$) was generated using p$C^{95-114}$-EGFP-$M^{1-40/YF.17D}$ as a template and the 3' primer 5'-AGAGTCGCGGCCGCAAATCAGGGGT-GCCTCAGGATCCATGT-CTCAATCTTTTGGAGTTGCC-3' (SEQ ID NO: 27) extended by 21 nucleotides to include a stop codon (TGA) followed by a NotI restriction site. Mutant protein $C^{95-114}$-EGFP-$M^{1-40/DEN-2}$ ($F^{36}$) was generated using p$C^{95-114}$-EGFP-$M^{1-40/DEN-2}$ as a template and the 3' primer 5'-TAGAGTCGCG-GCCGCGAATCATGGATGTCTCAAGAACCAAGTTTC-3' (SEQ ID NO:28) extended by 21 nucleotides to include a stop codon (TGA) followed by a NotI restriction site.

1.2) Methods

Flow Cytometry Analysis of Early Apoptosis

Apoptotic assays were carried out by surface staining with the $Ca^{2+}$-dependent phosphatidylserine (PS)-binding protein Annexin V. Transfected HeLa cells were labeled by incubation with Annexin V-APC (BD Pharmingen BioSciences), and 5 µg/ml of propidium iodide (PI) (Sigma) in a HEPES-based buffer (140 mM NaCl, 2.5 mM $CaCl_2$, 10 mM HEPES [pH 7.4]) for 15 min on ice according to the manufacturer's instructions. The stained cells were analyzed in a FACS-Calibur (Becton-Dickinson) using CellQuest 3.3 software.

Other Methods (See Example 1)

2) Results

Figure 4B:
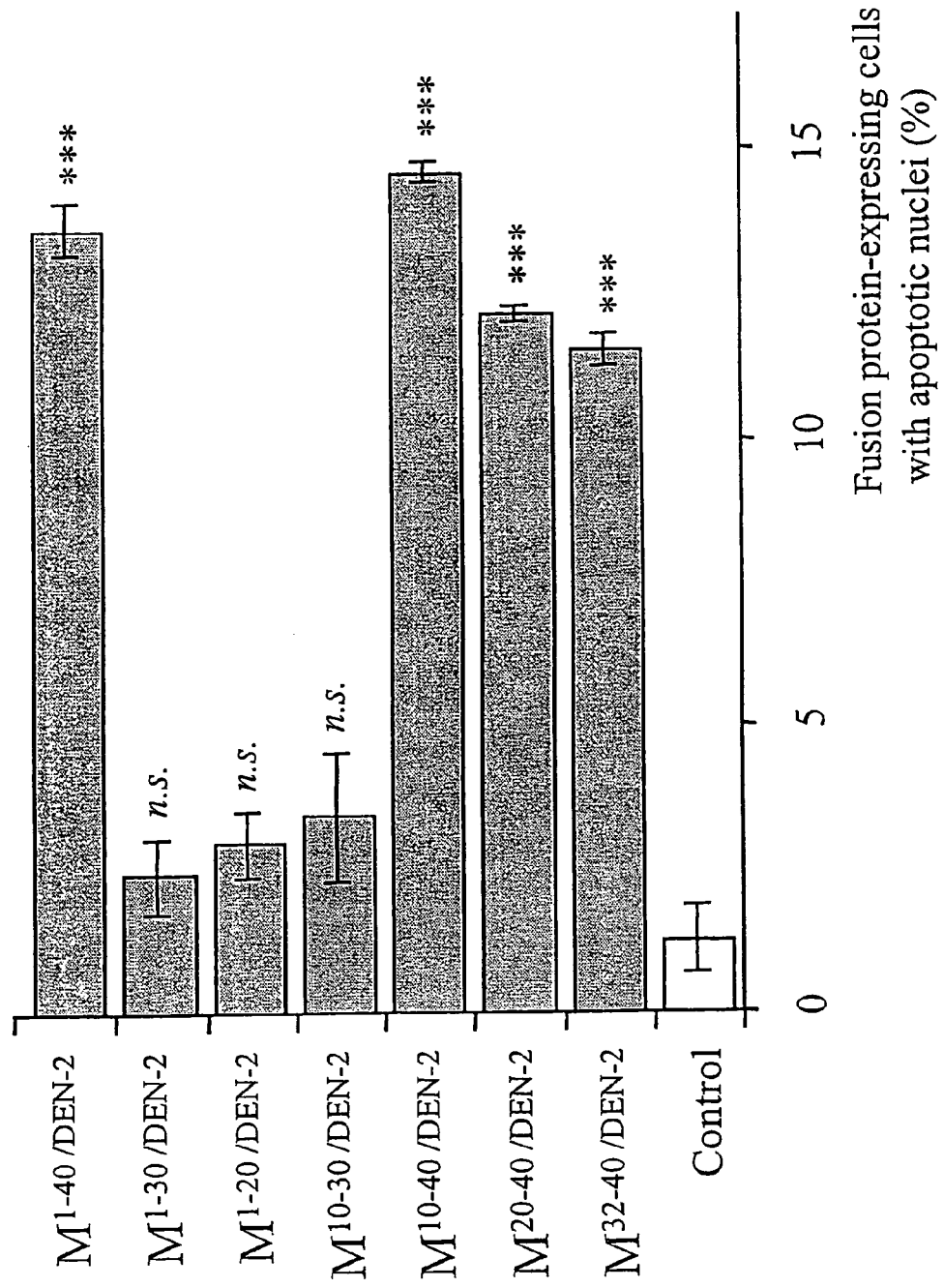

The Inventors tried to identify the amino acid residues critical for the death-promoting activity more precisely, using a series of fusion proteins consisting of EGFP fused to truncations from both ends of the 40-amino acid ectodomain of the DEN-2 M protein. The amino acid sequences of the mutant proteins are given in FIG. 4A. The apoptotic effects of the mutant proteins were assessed in HeLa cells after 25 hours of transfection. The production of truncated ecto-M mutant proteins containing only the first 30 amino acids of the DEN-2 ecto-M caused no CPEs in transfected HeLa cells (FIG. 4B). Thus, the amino-terminal part of ecto-M is not required for the induction apoptosis. The production of mutant proteins containing residues M-30 to M-40 induced apoptotic changes in nuclei (FIG. 4B), suggesting that the last amino acids are involved in the induction of apoptosis.

Figure 4C:
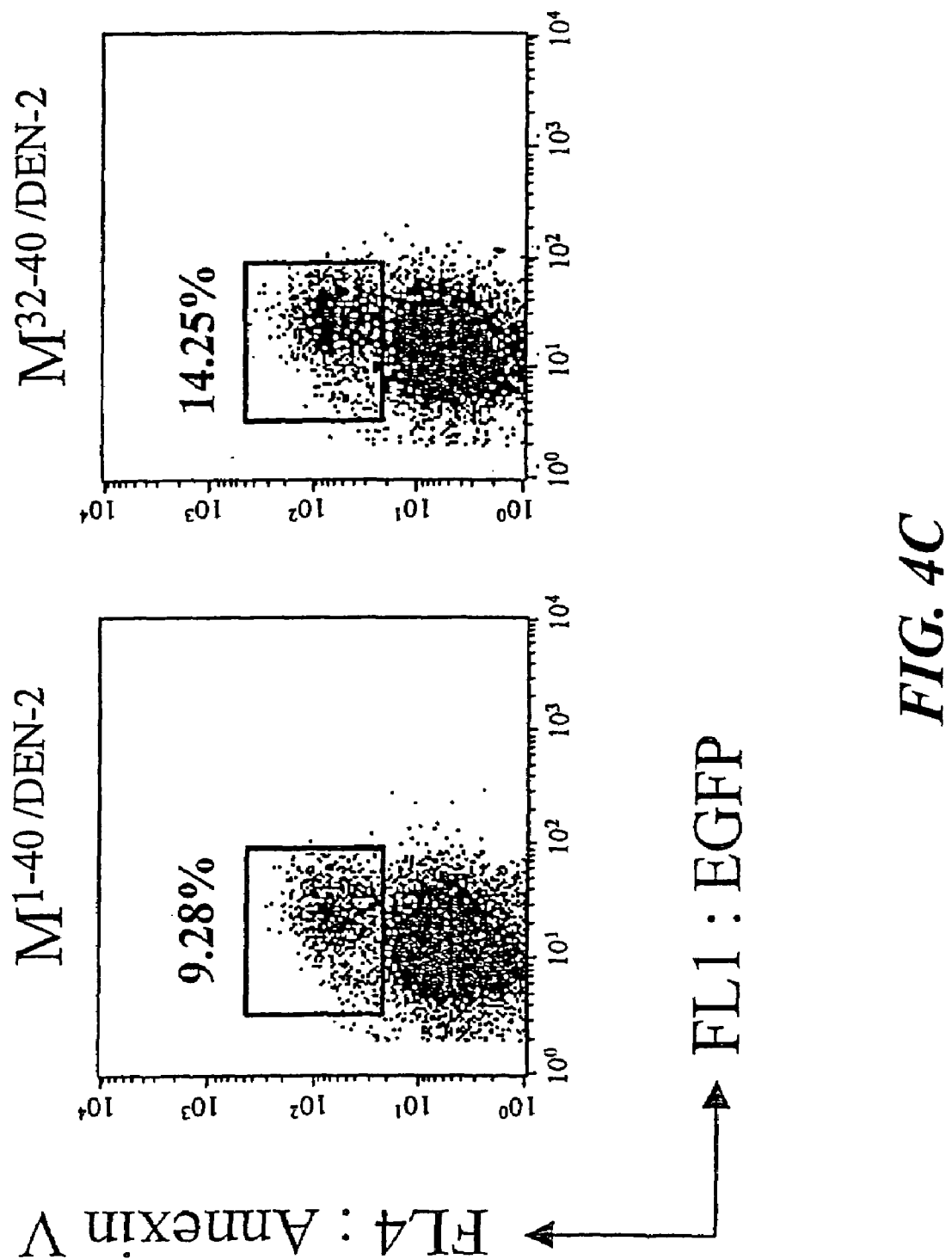

With a view to identifying the minimal sequence of the DEN-2 M ectodomain responsible for the induction of apoptosis, a construct encoding the 9 carboxy-terminal amino acids located at positions 32 to 40 fused to EGFP was engineered (FIG. 4A). The Inventors have investigated $M^{32-40/DEN-2}$-mediated cell death by flow cytometry, using the Annexin V affinity assay, which detects phosphatidylserine (PS) translocated to the outer layer of the cell membrane. The exposure of membrane PS is an early indicator of apoptosis. The fusion proteins $C^{95-114}$-EGFP-$M^{1-30/DEN-2}$ and $C^{95-114}$-EGFP-$M^{1-40/DEN-2}$ were used as negative and positive controls, respectively. In 3 independent experiments, the transfected HeLa cells producing $C^{95-114}$-EGFP-$M^{32-40/DEN-2}$ displayed significantly higher fraction of EGFP-positive cells labeled with Annexin V-APC that did cells producing $C^{95-14}$-EGFP-$M^{1-40/DEN-2}$ (FIG. 4C, squares). Thus, residues $^{32}$IETWALRHP$^{40}$ (SEQ ID NO:32–40 of SEQ ID NO:23) are responsible for the death-promoting activity of DEN-2 ecto-M. HeLa cells producing $C^{95-114}$-tagged EGFP and $C^{95-114}$-EGFP-$M^{1-30/DEN-2}$ also contained a subpopulation of Annexin V-labeled cells (FIG. 4C). It is likely that overproduction of EGFP has cytotoxic effects.

Figure 5:
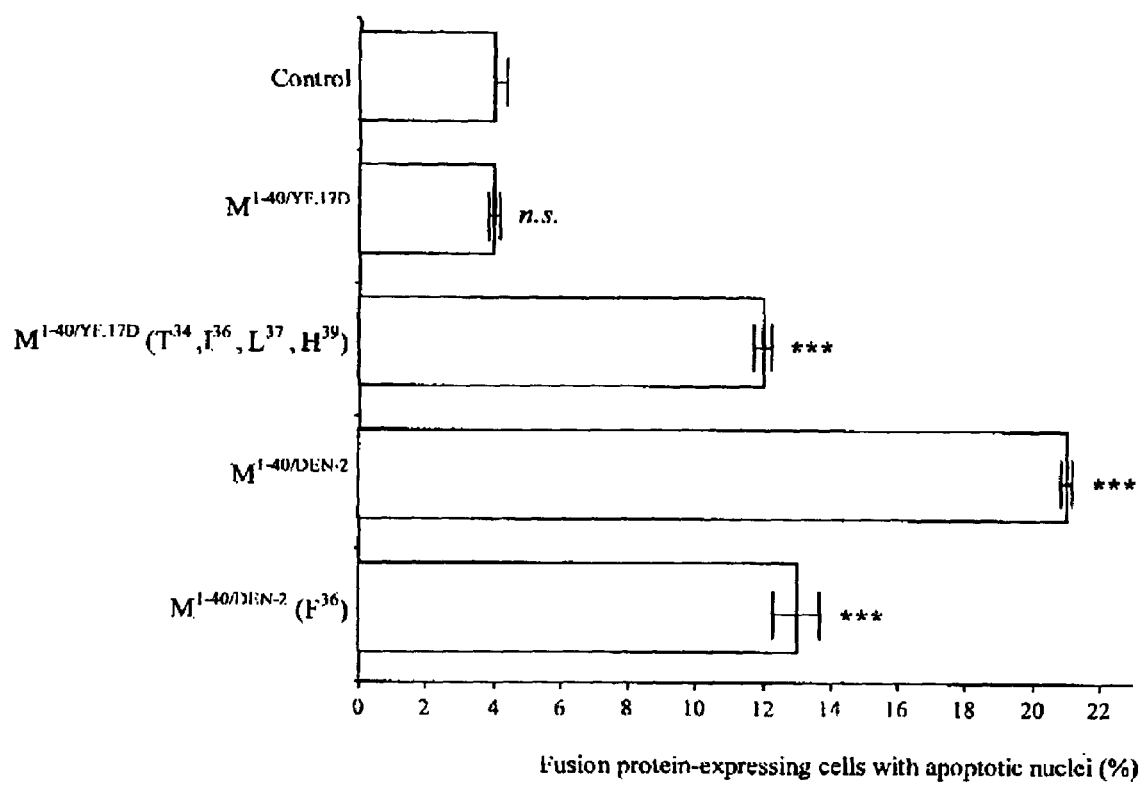

The Inventors have investigated whether the nine carboxy-terminal amino acids of the DEN-2 M ectodomain are potent in triggering apoptosis by introducing the substitutions $R^{34}T$, $L^{36}I$, $V^{37}L$ and $N^{39}H$ into the EGFP-tagged $M^{1-40/YF.17D}$ which had lost its cytotoxicity (FIG. 5A). The resulting mutant protein $C^{95-114}$-EGFP-$M^{1-40/YF.17D}$ ($T^{34}$, $I^{36}$, $L^{37}$, $H^{39}$) provokes apoptosis in transfected HeLa cells (FIG. 5B), narrowing down the region responsible for the death-promoting activity of DEN-2 ecto-M to residues M-34 to M-39.

The effect of the $F^{36}$ mutation on the death-promoting activity of DEN ecto-M was evaluated by generating a fusion protein, $C^{95-114}$-EGFP-$M^{1-40/DEN-2}$ ($F^{36}$), with a phenylalanine residue in position 36 of the DEN-2 M ectodomain (FIG. 5A). In transfected HeLa cells, the resulting mutant protein $C^{95-114}$-EGFP-$M^{1-40/DEN-2}$ ($F^{36}$) induced apoptosis significantly less efficiently than $M^{1-40/DEN-2}$ (FIG. 5B). The overall apoptosis-inducing activity of the M ectodomain reflected the intrinsic proapoptotic properties of residues M-32 to M-40, and the substitution of a leucine (YF ecto-M) or an isoleucine (DEN-2 ecto-M) for the phenylalanine in position M-36 can affect these properties.

REFERENCES

1. Adams J. M. et al., *Trends Biochem. Sci.*, 2001, 26: 61–66.
2. Adrain C. et al., *Trends Biochem. Sci.*, 2001, 26:390–397.
3. Bray M. et al., *Virology*, 1991, 185: 505–508.
4. Burns T. F. et al., *J. Cell. Physiol.*, 1999, 181: 231–239.
5. Chambers T. J. et al., *Annu. Rev. Microbiol.*, 1990, 44: 649–688.
6. Cocquerel L. et al., *J. Virol.*, 1999, 73: 2641–2649.
7. Courageot M-P. et al., *J. Virol.*, 2000, 74: 564–572.
8. Couvelard A. et al., *Hum. Pathol.*, 1999, 30: 1106–1110.
9. Desagher S. et al., *Trends Cell Biol.*, 2000, 10: 369–377.
10. Desprès P. et al., *J. Gen. Virol.*, 1987, 68: 2245–2247.
11. Desprès P. et al., *Virology*, 1993, 196: 209–219.
12. Desprès P. et al., *J. Virol.*, 1996, 70: 4090–4096.
13. Desprès P. et al., *J. Virol.*, 1998, 72: 823–829.
14. Duarte dos Santos C. N. et al., *Virology*, 2000, 274: 292–308.
15. Earnshaw W. C. et al., *Annu. Rev. Biochem.*, 1999, 68: 383–424.
16. Fearnhead H. O. et al., *Genes Dev.*, 1997, 11: 1266–1276.
17. Ferry, K. F. et al., *Nature Cell. Biol.*, 2001, 3: 255–263.
18. Gluzman Y., *Cell*, 1981, 23: 175–182.
19. Grabenhorst E. et al., *J. Biol. Chem.*, 1999, 274: 36107–36116.
20. Hahn, C. S. et al., *Proc. Natl. Acad. Sci.*, 1987, 84: 2019–2023.
21. Hengartner M. O., *Nature*, 2000, 407: 770–776.
22. Jan, J-T. et al., *J. Virol.*, 2000, 74: 8680–8691.
23. Jürgensmeier J. M. et al., *Natl. Acad. Sci.*, 1998, 95: 4997–5002.
24. Kimura K. et al., *Vitam. Horm.*, 2000, 58: 257–266.
25. Kuhn R. J. et al., *Cell*, 2002, 108: 717–725.
26. Kuwana T. et al., *Cell*, 2002, 111: 331–342.
27. Li P. et al., *Cell*, 1997, 91: 479–489.
28. Liao C-L. et al., *J. Virol.*, 1997, 71: 5963–5971.
29. Liao C-J. et al., *J. Virol.*, 1998, 72: 9844–9854.
30. Lin, Y-L. et al., *J. Med. Virol.*, 2000, 60: 425–431.
31. Lomonosova E. et al., *J. Virol.*, 2002, 76: 11283–11290.
32. Louis N. et al., *Virology*, 1997, 233: 423–429.
33. Marianneau P. et al., *J. Virol.*, 1997, 71: 3244–3249.
34. Marianneau P. et al., *J. Infect. Dis.*, 1998, 178: 1270–1278.
35. Monath T. P., 1999, *Yellow fever virus* (Flaviviridae), p1979–1986. In Encyclopedia of Virology, $2^d$ ed. Editors: Granoff, A. and Webster, R. G. Academic Press.
36. Parquet M. D. C. et al., *FEBS Lett.*, 2001, 500: 17–24.
37. Parquet M. C. et al., *Arch. Virol.*, 2002, 147: 1105–1119.
38. Pelham H. R., *Cell Struct. Funct.*, 1996, 21: 413–419.
39. Prikhod'ko G. G. et al., *Virology*, 2001, 286: 328–335.
40. Prikhod'ko G. G. et al., *J. Virol.*, 2002, 76: 5701–5710.
41. Rice C. M., 1996, Flaviviridae: the viruses and their replication, p.931–959. In Fields virology, $3^d$ ed. Editors: Fields, B. N., Knipe, D. M., Howley, P. M., et al. Lippincott-Raven Publishers, Philadelphia.
42. Roulston, A. et al., *Annu. Rev. Microbiol.*, 1999, 53, 577–628.
43. Slee E. A. et al., *J. Cell. Biol.*, 1999, 144: 281≧292.
44. Su H-L. et al., *Virology*, 2001, 282: 141–153.
45. Su H-L. et al., *J. Virol.*, 2002, 76: 4162–4171.
46. Tsai S-C. et al., *J. Biol. Chem.*, 2000, 275: 3239–3246.
47. Vazquez S. et al., *Vaccine*, 2002, 20: 1823–1830.
48. White E., *Oncogene*, 2001, 20: 7836–7846.
49. Wang E. et al., *J. Gen. Virol.*, 1995, 76: 2749–2755.
50. Xiao S-Y. et al., *J. Infect. Dis.*, 2001, 183: 1437–1444.
51. Yang J. et al., *Science*, 1997, 275: 1129–1132.
52. Ying H. et al., *J. Immunol.*, 1995, 154: 2743–2752.
53. Higgins D. et al., *Nucleic Acids Res.*, 1994, 22, 4673–4680.
54. R. Lopez et al., *The ClustalWWW server at the EBIembnet.news*, 1997, 4.2.
55. B. Levine et al., *Nature*, 1993, 361(6414), 739–42.
56. L. Ravagnan et al., *J. Cell. Physiol.*, 2002, 192, 131–137.

```
                              SEQUENCE LISTING

<160> NUMBER OF SEQ ID NOS: 36

<210> SEQ ID NO 1
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 1
gacaaacgtt ccgtggctct gtgacacacg tgggacttgg tctag                  45

<210> SEQ ID NO 2
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 2
ctattcccag cggccgctag gccattgatg gtg                                33

<210> SEQ ID NO 3
<211> LENGTH: 35
<212> TYPE: DNA
<213> ORGANISM: Artificial Sequence
<220> FEATURE:
```

<223> OTHER INFORMATION: synthetic oligonucleotide

<400> SEQUENCE: 3
cacagaagac tgtacagatc agtggcactc gttcc                                    35

<210> SEQ ID NO 4
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 4
atattcctag cggccgctat gtcattgaag gagcg                                    35

<210> SEQ ID NO 5
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 5
agacgcgtgt acagatcagt ggcgttagct ccccatgtcg cc                            42

<210> SEQ ID NO 6
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 6
gtttccgcgg ccgccacatc ttcatgtcat aggtgggta acc                            43

<210> SEQ ID NO 7
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 7
agacgagtgt acagctcagt agctttaaca ccacattcgg                               40

<210> SEQ ID NO 8
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 8
tgtttccgcg gccgccgcat cgtcatccgt aggatggggc ga                            42

<210> SEQ ID NO 9
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 9
aagcgaatgt acagatccgt gtcggtccaa acacatgggg agag                          44

```
<210> SEQ ID NO 10
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 10
attgccgcgg ccgcgacaat ttcaactgta agccggagcg acc              43

<210> SEQ ID NO 11
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 11
agacgcatgt acaggtcact gacagtgcag                              30

<210> SEQ ID NO 12
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 12
cattccgcgg ccgctctagc tgtaagctgg                              30

<210> SEQ ID NO 13
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 13
aggaggttgt acagggccat tgacttgcct acgcatgaaa acc               43

<210> SEQ ID NO 14
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 14
tgtcagtgcg gccgctgcag tgtcatgagt aggccggacc aac               43

<210> SEQ ID NO 15
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 15
ttttggcagt acatcaatgg gcg                                     23

<210> SEQ ID NO 16
<211> LENGTH: 38
<212> TYPE: DNA
<213> ORGANISM: Artificial Sequence
<220> FEATURE:
<223> OTHER INFORMATION: synthetic oligonucleotide
```

```
<400> SEQUENCE: 16
aagatcgcgg ccgcaattca ctggacatgt ttccaggc                              38

<210> SEQ ID NO 17
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 17
tttccgcggc cgctctgatc acatccatgt ttcagttcag                            40

<210> SEQ ID NO 18
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 18
tggttctgta catgggaatg ggactggaga cacg                                  34

<210> SEQ ID NO 19
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 19
tcttgcagtt cattcagggc accg                                             24

<210> SEQ ID NO 20
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 20
actgaaatgt acatgtcatc agaaggggcc tgg                                   33

<210> SEQ ID NO 21
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 21
atgtcctgta cattgaaact tggatcttga g                                     31

<210> SEQ ID NO 22
<211> LENGTH: 9
<212> TYPE: PRT
<213> ORGANISM: Artificial Sequence
<220> FEATURE:
<223> OTHER INFORMATION: synthetic peptide derived from DEN-2
<220> FEATURE:
<221> NAME/KEY: misc_feature
<222> LOCATION: (1)..(1)
<223> OTHER INFORMATION: Xaa is absent or present and represents A, V,
      L, I, P, F, W, M, C, G, S, T, Y, N or Q
<220> FEATURE:
<221> NAME/KEY: misc_feature
<222> LOCATION: (2)..(2)
```

```
<223> OTHER INFORMATION: Xaa is absent or present and represents D, E,
      A, V, L, I, P, F, W, M, C, G, S, T, Y, N or Q
<220> FEATURE:
<221> NAME/KEY: misc_feature
<222> LOCATION: (3)..(3)
<223> OTHER INFORMATION: Xaa is K, R, HA,V , L, I, P, F, W, M, C, G, S,
      T, Y, N or Q
<220> FEATURE:
<221> NAME/KEY: misc_feature
<222> LOCATION: (5)..(5)
<223> OTHER INFORMATION: Xaa is any amino acid except A, L or I
<220> FEATURE:
<221> NAME/KEY: misc_feature
<222> LOCATION: (6)..(6)
<223> OTHER INFORMATION: Xaa is A, V, L, I, P, F, W, M, or C
<220> FEATURE:
<221> NAME/KEY: misc_feature
<222> LOCATION: (7)..(7)
<223> OTHER INFORMATION: Xaa is K, R, or H
<220> FEATURE:
<221> NAME/KEY: misc_feature
<222> LOCATION: (8)..(8)
<223> OTHER INFORMATION: Xaa is K, R, H, G, S, T, Y, N, or Q
<220> FEATURE:
<221> NAME/KEY: misc_feature
<222> LOCATION: (9)..(9)
<223> OTHER INFORMATION: Xaa is absent or present and is K, R, H, A, V,
      L, I, P, F, W, M, or C

<400> SEQUENCE: 22

Xaa Xaa Xaa Trp Xaa Xaa Xaa Xaa Xaa
1               5

<210> SEQ ID NO 23
<211> LENGTH: 39
<212> TYPE: PRT
<213> ORGANISM: Dengue virus

<400> SEQUENCE: 23

Ser Val Ala Leu Val Pro His Val Gly Met Gly Leu Glu Thr Arg Thr
1               5                   10                  15

Glu Thr Trp Met Ser Ser Glu Gly Ala Trp Lys His Gln Arg Ile Glu
            20                  25                  30

Thr Trp Ile Leu Arg His Pro
        35

<210> SEQ ID NO 24
<211> LENGTH: 40
<212> TYPE: PRT
<213> ORGANISM: Dengue virus

<400> SEQUENCE: 24

Ala Ile Asp Leu Pro Thr His Glu Asn His Gly Leu Lys Thr Arg Gln
1               5                   10                  15

Glu Lys Trp Met Thr Gly Arg Met Gly Glu Arg Gln Leu Gln Lys Ile
            20                  25                  30

Glu Arg Trp Phe Val Arg Asn Pro
        35                  40

<210> SEQ ID NO 25
<211> LENGTH: 40
<212> TYPE: PRT
<213> ORGANISM: Dengue virus

<400> SEQUENCE: 25

Ala Ile Asp Leu Pro Thr His Glu Asn His Gly Leu Lys Thr Arg Gln
1               5                   10                  15
```

```
Glu Lys Trp Met Thr Gly Arg Met Gly Glu Arg Gln Leu Gln Lys Ile
            20                  25                  30
Glu Thr Trp Ile Leu Arg His Pro
        35                  40
```

<210> SEQ ID NO 26
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 26
agagtcgcgg ccgcaaatca ggggttcctc ccaaccatct ctc        43

<210> SEQ ID NO 27
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 27
agagtcgcgg ccgcaaatca ggggtgcctc aggatccatg tctcaatctt ttggagttgc     60
c                                                                    61

<210> SEQ ID NO 28
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 28
tagagtcgcg gccgcgaatc atggatgtct caagaaccaa gtttc        45

<210> SEQ ID NO 29
<211> LENGTH: 39
<212> TYPE: PRT
<213> ORGANISM: Dengue virus

<400> SEQUENCE: 29

```

<213> ORGANISM: Dengue virus

<400> SEQUENCE: 31

Met Asn Arg Arg Lys Arg Ser Val Thr Met Leu Leu Met Leu Leu Pro
1               5 10 15

Thr Ala Leu Ala Arg Asp Pro Pro Val Ala Thr Met
20 25

<210> SEQ ID NO 32
<211> LENGTH: 91
<212> TYPE: DNA
<213> ORGANISM: Artificial Sequence
<220> FEATURE:
<223> OTHER INFORMATION: recombinant plasmid vector sequence

<400> SEQUENCE: 32
gctagcaatg aacaggagga aaagatccgt gaccatgctc ctcatgctgc tgcccacagc 60
cctggcccgg gatccaccgg tcgccaccat g 91

<210> SEQ ID NO 33
<211> LENGTH: 8
<212> TYPE: PRT
<213> ORGANISM: Dengue virus

<400> SEQUENCE: 33

Leu Ala Met Glu Glu Leu Tyr Asn
1 5

<210> SEQ ID NO 34
<211> LENGTH: 42
<212> TYPE: DNA
<213> ORGANISM: Artificial Sequence
<220> FEATURE:
<223> OTHER INFORMATION: recombinant plasmid vector sequence

<400> SEQUENCE: 34
ctcggcatgg acgagctgta caagtaaagc ggccgcactc ta 42

<210> SEQ ID NO 35
<211> LENGTH: 48
<212> TYPE: PRT
<213> ORGANISM: Dengue virus

<400> SEQUENCE: 35

Leu Ala Met Glu Glu Leu Tyr Arg Ser Val Ala Leu Val Pro His Val
1 5 10 15

Gly Met Gly Leu Glu Thr Arg Thr Glu Thr Trp Met Ser Ser Glu Gly
20 25 30

Ala Trp Lys His Val Gln Arg Ile Glu Thr Trp Phe Leu Arg His Pro
35 40 45

<210> SEQ ID NO 36
<211> LENGTH: 70
<212> TYPE: DNA
<213> ORGANISM: Artificial Sequence
<220> FEATURE:
<223> OTHER INFORMATION: recombinant plasmid vector sequence

<400> SEQUENCE: 36
ctcggcatgg acgagctgta cagatcagtg gcactcgttt tcttgagaca tccatgagcg 60
gccgcgactc 70

The invention claimed is:

1. An isolated and purified peptide consisting of 6–9 consecutive amino acids of residues 32–40 of a dengue virus M protein ectodomain, wherein the amino acid at position 36 of said ectodomain is substituted with phenylalanine.

2. The peptide of claim 1, wherein said dengue virus M protein ectodomain is from serotype 1.

3. The peptide of claim 1, wherein said dengue virus M protein ectodomain is from serotype 2.

4. The peptide of claim 1, wherein said dengue virus M protein ectodomain is from serotype 3.

5. The peptide of claim 1, wherein said dengue virus M protein ectodomain is from serotype 4.

6. The peptide of claim 1, which consists of 6 or 7 amino acids.

7. The peptide of claim 1, which consists of 8 or 9 amino acids.

8. The peptide of claim 1, in which an L-amino acid has been replaced by a D-amino acid or where a glutamine has been replaced with a pyroglutamic acid.

9. The peptide of claim 1, which has been conjugated to an immunogenic carrier.

10. The peptide of claim 1, which has been conjugated to BSA.

11. The peptide of claim 1, which has been conjugated to KLH.

12. A multimer of the peptide of claim 1.

13. A fusion protein comprising the peptide of claim 1 and an exogenous, non-dengue virus M protein, polypeptide.

14. The peptide of claim 1 which is attached to a support.

15. A method for the serological detection of a flavivirus infection comprising:
   contacting a biological sample with a solid support to which the peptide of claim 1 which has been bound, and
   detecting the formation of peptide-antibody complexes, wherein the formation of an peptide-antibody complex is indicative of flavivirus infection.

* * * * *